US009138196B2

(12) United States Patent
Zhu

(10) Patent No.: US 9,138,196 B2
(45) Date of Patent: Sep. 22, 2015

(54) X-RAY COLLIMATOR FOR CT SYSTEM

(71) Applicant: Shenyang Neusoft Medical Systems Co., Ltd., Shenyang (CN)

(72) Inventor: Yiming Zhu, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 82 days.

(21) Appl. No.: 14/142,962

(22) Filed: Dec. 30, 2013

(65) Prior Publication Data
US 2015/0071411 A1    Mar. 12, 2015

(30) Foreign Application Priority Data

Sep. 10, 2013   (CN) .......................... 2013 1 0410350

(51) Int. Cl.
*A61B 6/06*   (2006.01)
*G21K 1/04*   (2006.01)
*G21K 1/02*   (2006.01)
*G02B 27/30*  (2006.01)

(52) U.S. Cl.
CPC . *A61B 6/06* (2013.01); *G02B 27/30* (2013.01); *G21K 1/04* (2013.01); *G21K 1/02* (2013.01)

(58) Field of Classification Search
CPC ............... G02B 27/09; G02B 27/0938; G02B 27/0988; G02B 27/30; G21K 1/00; G21K 1/02; G21K 1/04; G21K 1/046; A61B 6/06

USPC .......... 378/145, 147–152, 204, 210; 359/641
See application file for complete search history.

(56) References Cited

U.S. PATENT DOCUMENTS 6,441,377 B1 *   8/2002   Hug et al. ................. 250/363.1
2014/0146949 A1 *  5/2014   Pan et al. ...................... 378/152

FOREIGN PATENT DOCUMENTS

CN            102467985 A      5/2012

* cited by examiner

*Primary Examiner* — Anastasia Midkiff
(74) *Attorney, Agent, or Firm* — Kilpatrick Townsend & Stockton LLP

(57) ABSTRACT

An X-ray collimator used in a CT system is provided, including: a first guide rail and a second guide rail disposed in parallel with each other; and a first gate assembling unit and a second gate assembling unit disposed in parallel with each other. The first gate assembling unit has one end provided with a driving mechanism and fixedly connected with the first guide rail, and another end connected with the second guide rail in a slidable connection. The second gate assembling unit has one end provided with a driving mechanism and fixedly connected with the second guide rail, and another end connected with the first guide rail in a slidable connection. And blocks for supporting and position limiting are provided on two ends of the first guide rail and two ends of the second guide rail. Sheltering effect on X-rays may be improved.

12 Claims, 5 Drawing Sheets

X-RAY COLLIMATOR FOR CT SYSTEM

CROSS REFERENCE TO RELATED APPLICATIONS

The present application claims priority to Chinese Patent Application No. 201310410350.0, filed on Sep. 10, 2013 and entitled "X-RAY COLLIMATOR FOR CT SYSTSEM", the entire disclosure of which is incorporated herein by reference.

FIELD OF THE DISCLOSURE

The present disclosure generally relates to medical facilities, and more particularly, to an X-ray collimator for a CT system.

BACKGROUND OF THE DISCLOSURE

Basic components and working principles of a Computed Tomography (CT) system are illustrated as follows.

The CT system has a scanner gantry in which a rotation device is equipped. The rotation device is mounted with an X-ray tube, an X-ray collimator and an X-ray detector. In a chamber defined by the scanner gantry, there is provided a patient table. A target object may lie on the patient table, while the rotation device is rotating around the target object. As such, the X-ray tube can irradiate the target object from different angles. The X-ray detector may receive the X-rays which are emitted from the X-ray tube and attenuated when passing through the target object, and obtain corresponding data based on the attenuated X-ray's. CT images may be rebuilt after the data is processed with a computer.

During the X-ray scanning process, the X-ray collimator is normally disposed between the X-ray tube and the target object, which may be beneficial for reducing influence from scattered rays and further improving image quality. The X-ray collimator may control the emitting range and direction of the X-ray beams. By partially sheltering the emitted X-rays, the X-ray collimator can control the X-rays from the tube to irradiate the target object through a specific gap.

Chinese patent application No. 201010543278.5 discloses an X-ray collimator which includes two gates for defining a gap. However, only one of the two gates can be moved to adjust the width of the gap, that is, the width of the gap can only be adjusted in a small range. Therefore, an X-ray collimator which can provide better sheltering effect on the X-rays is required.

BRIEF SUMMARY OF THE DISCLOSURE

Embodiments of the present disclosure provide an X-ray collimator used in a CT system to improve sheltering effect on the X-ray.

According to one embodiment, an X-ray collimator used in a CT system is provided, the collimator includes:

a first guide rail and a second guide rail disposed in parallel with each other; and a first gate assembling unit and a second gate assembling unit disposed in parallel with each other, wherein the first gate assembling unit has one end provided with a driving mechanism and fixedly connected with the first guide rail, and another end connected with the second guide rail in a slidable connection, wherein the second gate assembling unit has one end provided with a driving mechanism and fixedly connected with the second guide rail, and another end connected with the first guide rail in a slidable connection, wherein blocks for supporting and position limiting are provided on two ends of the first guide rail and two ends of the second guide rail.

Optionally, the first guide rail and the second guide rail are linear axis, and the slidable connections are implemented by using linear bearings.

Optionally, the first guide rail and the second guide rail are linear guide rails, and the slidable connections are implemented by using slidable blocks.

Optionally, each of the first gate assembling unit and the second gate assembling unit comprises a base mounted with a slot and a board corresponding with the slot.

Optionally, the base is provided with fixing components for fixing the board.

Optionally, the bases of the first gate assembling unit and the second gate assembling unit are provided with blocks respectively disposed on opposing inner sides of the first gate assembling unit and the second gate assembling unit.

Optionally, the board is an arc plate or a flat plate.

Optionally, the bases of the first gate assembling unit and the second gate assembling unit are provided with baffle plates respectively disposed on outer sides of the bases of the first gate assembling unit and the second gate assembling unit, where the outer sides are opposite to opposing inner side of the bases of the first gate assembling unit and the second gate assembling unit.

Optionally, the board comprises at least one material selected from a group consisting of W, Mo and Ta.

Optionally, the base comprises aluminum alloy or steel.

Optionally, the fixing components comprise:

at least one threaded hole provided in the base and at least one corresponding blot for pressing the board.

Optionally, the fixing components comprise:

at least one fixing block for pressing and fixing the board, at least one threaded hole provided in the base and at least one corresponding blot for pressing the at least one fixing block.

Compared with conventional techniques, embodiments of the present disclosure may have following advantages.

The two gate assembling units are configured to be driven to move by driving mechanisms, respectively. Therefore, each of the two gate assembling units can do reciprocating motion along the length direction of the guide rails. The width and position of the gap defined between the two gate assembling units thus can be adjusted by controlling the movement of either gate assembling unit. If the two gate assembling units move in opposite directions, a larger gap width may be obtained, such that the adjustable width range of the gap is increased. If the two gate assembling traits move in a same direction, the position of the gap may be adjusted, such that the X-rays can irradiate the target object at a controllable position. Using the X-ray collimator of embodiments of the present disclosure, a wider adjustable gap width range may be obtained, and the X-ray irradiation position on the target object can be adjusted conveniently, so the sheltering effect on the X-rays may be improved.

Further, in embodiments of the present disclosure, each of the guide rails with a certain length may have its two ends mounted with blocks for supporting and position limiting, and fixedly connected with one end of a gate assembling unit. Besides, another end of the gate assembling unit may be connected with another guide rail in a slidable connection. Therefore, when the gate assembling unit is driven to move by the corresponding driving mechanism, its movement may be controlled by an effective and stable triangle structure formed by the two blocks, the slidable connecting point and the corresponding linear bearing. Thus, control of the movements of the gate assembling units may be more accurate and more stable, thereby further improving the sheltering effect of the X-ray collimator on the X-rays.

BRIEF DESCRIPTION OF THE DRAWINGS

In order to clarify the disclosure and advantages thereof, accompanying drawings used in description of embodiments of the present disclosure will be described simply. Obviously, drawings described below are only illustrative and those skilled in the art can obtain other drawings based on these drawings without creative works.

DETAILED DESCRIPTION OF THE DISCLOSURE

In order to clarify the objects, characteristics and advantages of the disclosure, embodiments of the disclosure will be interpreted in detail in combination with accompanied drawings. Apparently, embodiments illustrated below are merely examples, which should not limit the scope of the present disclosure. Those skilled in the art can make variations and modifications without creative work in light of the present disclosure, and those variations and modifications are in the scope of the present disclosure.

Figure 1:
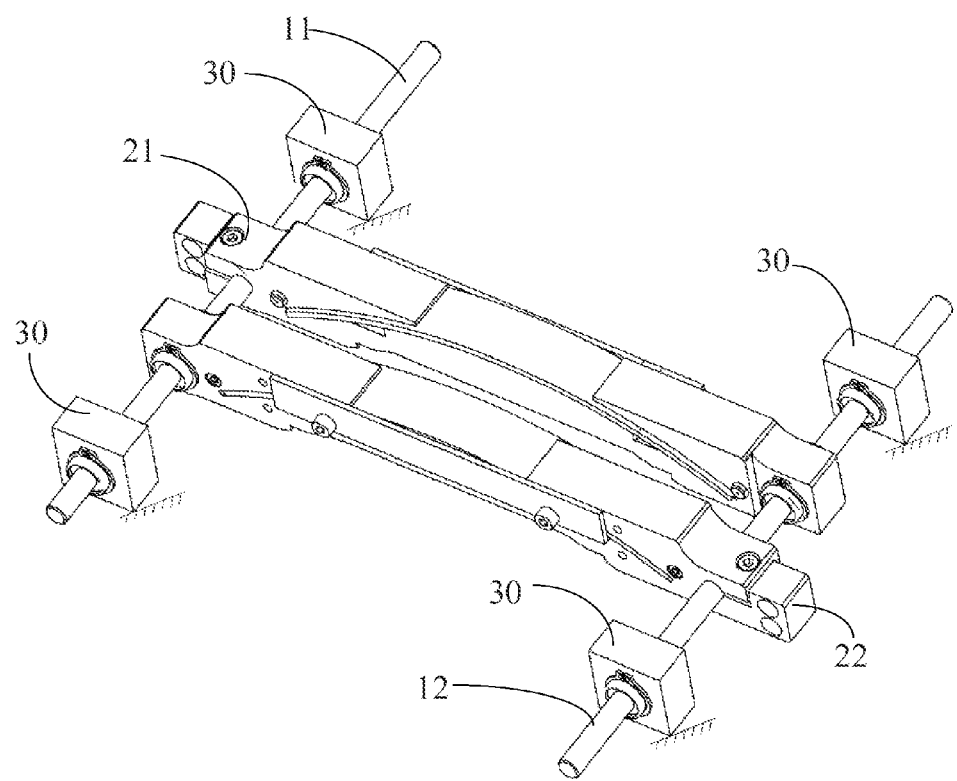
FIG. 1 schematically illustrates a three-dimensional view of an X-ray collimator for a CT system according to one embodiment of the present disclosure.

In order to improve sheltering effect on X-rays, an X-ray collimator for a CT system is provided according to one embodiment of the present disclosure. Referring to FIG. 1, the collimator includes: a first guide rail 11 and a second guide rail 12 which are disposed in parallel with each other; and a first gate assembling unit 21 and a second gate assembling unit 22 which are disposed in parallel.

The first gate assembling unit 21, provided with a driving mechanism, has one end fixedly connected with the first guide rail 11 and another end slidably connected with the second guide rail 12. The second gate assembling unit 22, provided with a driving mechanism, has one end fixedly connected with the second guide rail 12 and another end slidably connected with the first guide rail 11.

On two ends of both the first guide rail 11 and the second guide rail 12, there are mounted blocks 30 for supporting and position limiting.

The X-ray collimator may be disposed between an X-ray tube and a target object, such that the first gate assembling unit 21 and the second gate assembling unit 22 can block the X-rays. The first gate assembling unit 21 and the second gate assembling unit 22 may define a gap through which the X-rays may only irradiate the target object at a predetermined position, such that influence from scattered rays may be reduced and further image quality may be improved.

One end of the first gate assembling unit 21 is fixed to the first guide rail 11, while the other end thereof is slidably connected with the second guide rail 12. Driven by the driving mechanism, the first guide rail 11 may carry the first gate assembling unit 21 to do reciprocating motions along the length direction of the first guide rail 11, so as to adjust the width of the gap defined by the first gate assembling unit 21 and the second gate assembling unit 22. Since the motion of the first guide rail 11 is limited and supported by the two blocks 30 and the distance between the two blocks 30 is relatively long, the first gate assembling unit 21 fixedly connected with the first guide rail 11 can move more stably. Further, more accurate control of width of the gap may be achieved.

In practice, both the first guide rail 11 and the second guide rail 12 may be linear axis or linear guide rails.

If both the first guide rail 11 and the second guide rail 12 are linear axis, they may be slidably connected with the two gate assembling units through linear bearings 31, respectively. Specifically, the slidable connecting end of the first gate assembling unit 21 may be socket jointed with the second guide rail 12, such that the first gate assembling unit 21 can do reciprocating motions along the length direction of the second guide rail 12 through the linear bearing 31. Similarly, the slidable connecting end of the second gate assembling unit 22 may be socket jointed with the first guide rail 11, such that the second gate assembling unit 22 can do reciprocating motions along the length direction of the first guide rail 11 through the linear bearing 31.

In some embodiments, both the first guide rail 11 and the second guide rail 12 are linear guide rails. In such configurations, the slidable connection between the two guide rails and the two gate assembling units may be realized using slidable blocks. That is to say, the linear guide rails cooperate with the slidable blocks to implement the slidable connections between the guide rails and the gate assembling units.

Figure 2:
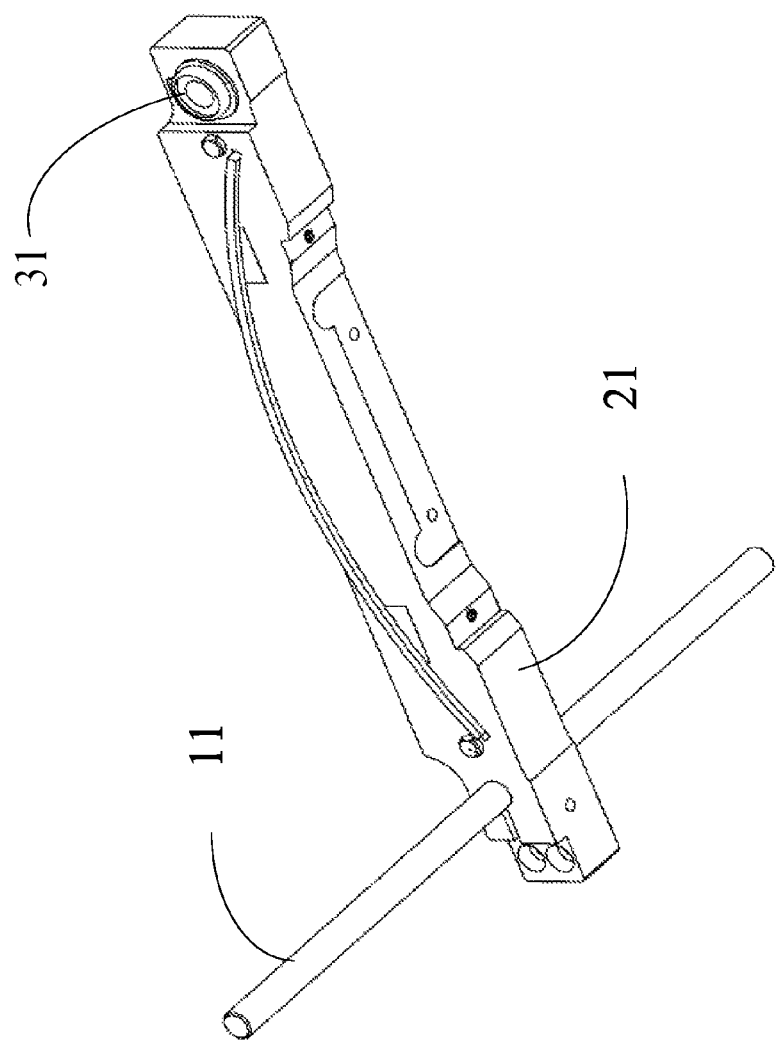
FIG. 2 schematically illustrates a three-dimensional view of a gate assembling unit according to one embodiment of the present disclosure.

Specifically, referring to FIG. 2, in Borne embodiments, the first guide rail 11 and the second guide rail 12 are linear axis. In such configurations, the first gate assembling unit 21 and the second guide rail 12 are connected through the linear bearing 31. Therefore, friction, which occurs when the first gate assembling unit 21 is sliding along the second guide rail 12, may be effectively reduced.

Similarly as the first gate assembling unit 21, after having one end fixedly connected with the second guide rail 12, the second gate assembling unit 22 may have the other end slidably connected with the first guide rail 11. As such, driven by the driving mechanism, the second guide rail 12 may carry the second gate assembling unit 22 to do reciprocating motions along the length direction of the second guide rail 12. Therefore, the width of the gap defined between the first gate assembling unit 21 and the second gate assembling unit 22 can be adjusted.

In some embodiments, the two ends of the first guide rail 11 may be connected with two blocks 30 through linear bearings or slidable blocks, and the two ends of the second guide rail 12 may be connected with two blocks 30 through linear bearings or slidable blocks.

In such configurations, each of the first gate assembling 21 and the second gate assembling unit 22 may be driven by a corresponding driving mechanism to move independently to adjust the width of the gap defined between the first gate assembling unit 21 and the second gate assembling unit 22. If the first gate assembling unit 21 and the second gate assembling unit 22 move in opposite directions, the width of the gap is a sum of moving distances of the first gate assembling unit 21 and the second gate assembling unit 22, such that the width of the gap may have a larger range, which is beneficial for enlarging the scanning area of the CT system.

If the first gate assembling unit 21 and the second gate assembling unit 22 move in a same direction, the position of the gap may be changed correspondingly, such that the controllability of the gap may be further improved. For example, the first gate assembling unit 21 and the second gate assembling unit 22 may move in a same direction along the first guide rail 11 or the second guide rail 12, which may result in the position of the gap being changed along the same direction. Such that, X-rays can irradiate the target object from different controllable positions.

Figure 3:
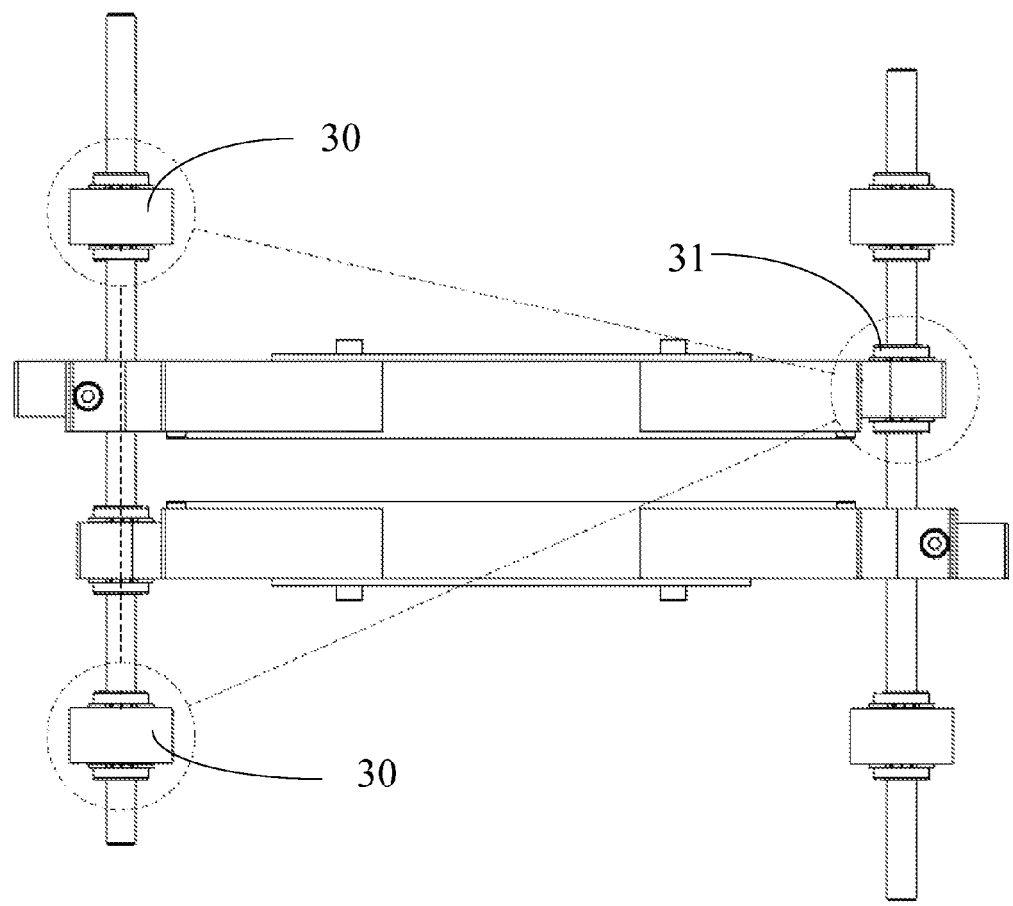
FIG. 3 schematically illustrates a top view of an X-ray collimator for a CT system according to one embodiment of the present disclosure.

Further, referring to FIG. 3, in embodiments of the present disclosure, each of the guide rails with a certain length may have its two ends mounted with blocks 30 for supporting and position limiting, and fixedly connected with one end of a gate assembling unit. Besides, another end of the gate assembling unit may be slidably connected with the other guide rail. Therefore, when the gate assembling unit is driven to move by the corresponding driving mechanism, its movement may be controlled by an effective and stable triangle structure formed by the two blocks 30, the slidable connecting point and the corresponding linear bearing 31. Thus, control of the movements of the gate assembling units may be more accurate and more stable, thereby further improving the sheltering effect of the X-ray collimator on the X-rays.

The X-ray collimators provided by embodiments of the present disclosure have a relatively simple structure and may occupy smaller space. Therefore, the space on the patient table for placing the target object may be enlarged whereby an acceptable variation in the size of the target object may be obtained for the CT system.

Figure 4:
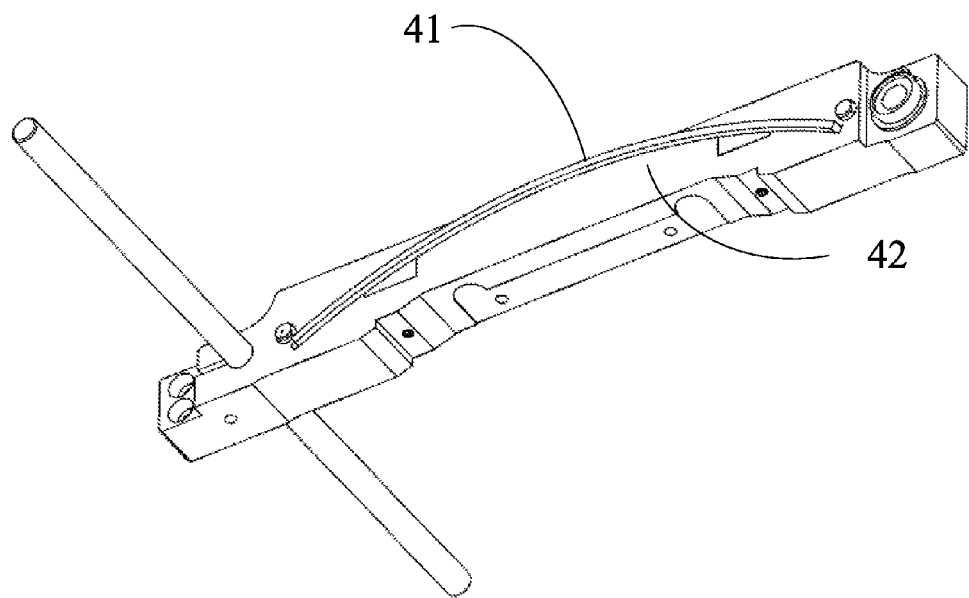
FIG. 4 schematically illustrates a three-dimensional view of a gate assembling unit according to one embodiment of the present disclosure.

In some embodiments, referring to FIG. 4, both the first gate assembling unit 21 and the second gate assembling unit 22 may include: a base 42 configured with a slot and a board 41 corresponding to the slot.

The boards 41 in both the first gate assembling unit 21 and the second gate assembling unit 22 may include at least one material selected from a group consisting of W, Mo and Ta, since only these specific materials can block the high frequency electromagnetic energy of X-rays. The bases 42 of both the first gate assembling unit 21 and the second gate assembling unit 22 may be used for fixing and accommodating the corresponding boards 41.

As mounting holes may cause radiation leakage, in some embodiments, there are no mounting holes configured on the board 41 for fixedly connecting with the base 42. Instead, the board 41 is inserted into the slot of the base 42 and fixed therein. Since the board 41 has no mounting holes, radiation leakage due to mounting holes may be avoided, thus improving the safety of the CT system.

Further, in the above described configurations, the board and the base constitute the gate assembling unit. As the base is only used for fixedly connecting the board, which is not required to block radiation, lighter and/or cheaper materials may be selected to form the base as long as the rigidity thereof is guaranteed. In some embodiments, the material of the base may be aluminum alloy, steel, or the like.

Normally, the base may have a relatively large size. Since lighter materials can be selected for forming the base, the reduction of the base weight may lead to an obvious effect on reducing the whole weight of the X-ray collimator. With a reduced weight, the X-ray collimator may have improved self-stability when rotating with the CT system at a relatively high speed. Vibrations may also be reduced. Therefore, scanning effect of the CT system may be improved.

In some embodiments, for further improve the stability of the connection between the board and the base, fixing components may be provided on the base for fixing the board.

There are various fixing components which are available and suitable. For example, at least one threaded holes may be provided in the base, and the board may be pressed tightly onto the base by tightening at least one corresponding bolt.

Figure 5:
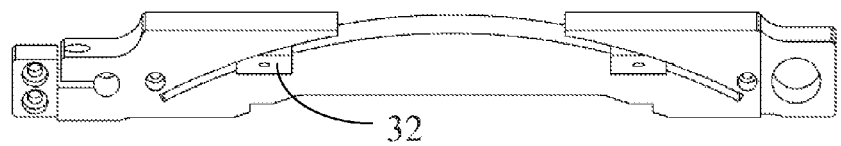
FIG. 5 schematically illustrates a three-dimensional view of a gate assembling unit according to one embodiment of the present disclosure.

In some embodiments, referring to FIG. 5, at least one fixing block 32 may be provided between the bolt and the board for further pressing and fixing the board. The bolt may press the fixing block 32 by tightening the bolt into the corresponding threaded hole disposed in the base. As a result, the fixing block 32 may press the board on the base, such that the board may be fixed on the base. The bolt may not press the board directly, but through the fixing block 32 with a lager contacting area, which may achieve a better fixing effect.

In some embodiments, the board may be an arc plate or a flat plate. Correspondingly, the slot of the base may have a size adapted for accommodate the board.

Figure 6:
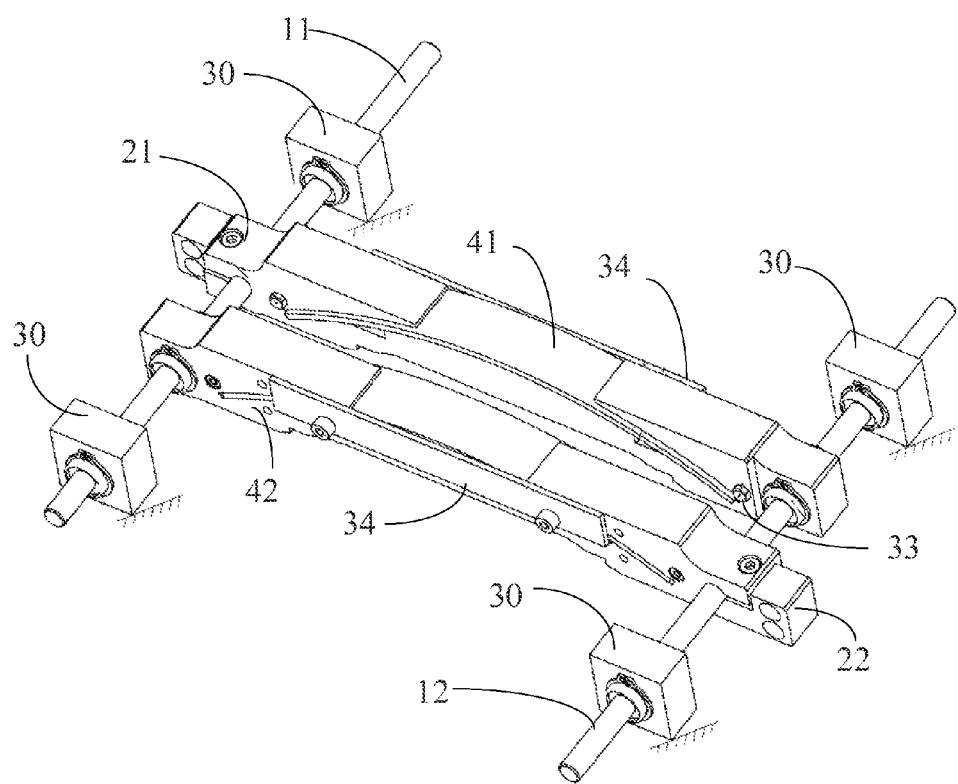
FIG. 6 schematically illustrates a three-dimensional view of an X-ray collimator for a CT system according to one embodiment of the present disclosure.

It could be understood that, since the first guide rail and the second guide rail, driven by corresponding driving mechanisms, respectively, may move the first and second gate assemblies closer to each other, there is a possibility for the first gate assembling unit 21 and the second gate assembling unit 22 colliding with each other due to an improper operation. Referring to FIG. 6, in some embodiments, to protect the first gate assembling unit 21 and the second gate assembling unit 22, avoid damages caused by collision and prevent influence on accuracy of the X-ray collimator, anti-collision blocks 33 for preventing collision between the gate assembling units may be provided on base 42 of the first gate assembling unit 21 and/or the second gate assembling unit 22. The blocks 33 may be disposed on either or both the opposing surfaces (inner sides) of the first gate assembling unit 21 and the second gate assembling unit 22, and may protrude from the opposing surfaces. Therefore, direct collision between the first gate assembling unit 21 and the second gate assembling unit 22 can be avoided, which may protect the machine.

Specifically, in some embodiments, the blocks 33 may be convex portions of the bases of the first gate assembling unit 21 and/or the second gate assembling unit 22. In some embodiments, the blocks 33 may be convex components mounted on the bases of the first gate assembling unit 21 and/or the second gate assembling unit 22, such as convex components attached on the base or fixed with the threaded hole of the base.

Further, for convenient assembly and disassembly of the board 41, in some embodiments, the slot may penetrate through two sides of the base 42. Therefore, the board 41 can be inserted into the slot from one side of the base 42 conveniently. For controlling and fixing the board 41, in some embodiments, baffle plates 34 may be provided on outer sides of the bases of the first gate assembling unit 21 and the second gate assembling unit 22, at positions covering the slots. The outer side of the first gate assembling unit is opposite to the inner side of the base of the first gate assembling unit, and the outer side of the second gate assembling unit is opposite to the inner side of the base of the second gate assembling unit. Therefore, when the boards 41 are inserted into the slots from the inner sides, respectively, the baffle plates 34 on the outer sides of the bases 42 may block the boards from moving outward.

Embodiments of the present disclosure are illustrated in a progressive way. Differences between embodiments are illustrated in detail. By referring to other embodiments, same and/or similar technical information can be obtained.

Although the present disclosure has been disclosed above with reference to preferred embodiments thereof, it should be understood that the disclosure is presented by way of example only, and not limitation. Those skilled in the art can modify and vary the embodiments without departing from the spirit and scope of the present disclosure.

What is claimed is:

1. An X-ray collimator for a CT system, comprising:
    a first guide rail and a second guide rail disposed in parallel with each other; and
    a first gate assembling unit and a second gate assembling unit disposed in parallel with each other,
    wherein the first gate assembling unit has one end fixedly connected with the first guide rail, and another end connected with the second guide rail in a slidable connection,
    wherein the second gate assembling unit has one end fixedly connected with the second guide rail, and another end connected with the first guide rail in a slidable connection,
    wherein blocks for supporting and position limiting are provided on two ends of the first guide rail and two ends of the second guide rail.

2. The X-ray collimator according to claim 1, wherein the first guide rail and the second guide rail are linear axis, and the slidable connections are implemented by using linear bearings.

3. The X-ray collimator according to claim 1, wherein the first guide rail and the second guide rail are linear guide rails, and the slidable connections are implemented by using slidable blocks.

4. The X-ray collimator according to claim 1, wherein each of the first gate assembling unit and the second gate assembling unit comprises a base mounted with a slot and a board corresponding to the slot.

5. The X-ray collimator according to claim 4, wherein the bases of the first gate assembling unit and the second gate assembling unit are provided with fixing components for fixing each of the boards in each of said slots.

6. The X-ray collimator according to claim 4, wherein the bases of the first gate assembling unit and the second gate assembling unit are provided with anti-collision blocks respectively disposed on opposing inner sides of the first gate assembling unit and the second gate assembling unit.

7. The X-ray collimator according to claim 4, wherein the boards of the first gate assembling unit and the second gate assembling unit are arc plates or flat plates.

8. The X-ray collimator according to claim 4, wherein the bases of the first gate assembling unit and the second gate assembling unit are respectively disposed on outer sides of the bases of the first gate assembling unit and the second gate assembling unit.

9. The X-ray collimator according to claim 4, wherein the boards of the first gate assembling unit and the second gate assembling unit comprise at least one material selected from a group consisting of W, Mo and Ta.

10. The X-ray collimator according to claim 4, wherein the bases of the first gate assembling unit and the second gate assembling unit comprise aluminum alloy or steel.

11. The X-ray collimator according to claim 5, wherein the fixing components for each of the first gate assembling unit and the second gate assembling unit comprise:
    at least one threaded hole provided in the base and at least one bolt for pressing the board.

12. The X-ray collimator according to claim 5, wherein the fixing components for each of the first gate assembling unit and the second gate assembling unit comprise:
    at least one fixing block for pressing and fixing the board, at least one threaded hole provided in the base and at least one corresponding bolt for pressing the at least one fixing block.

* * * * *